(12) United States Patent
Fischer Lokou (10) Patent No.: US 10,687,878 B2
(45) Date of Patent: Jun. 23, 2020

(54) IMPLANT FOR THE FIXATION OF BONE ELEMENTS

(71) Applicant: David François Fischer Lokou, Oberschaeffolsheim (FR)

(72) Inventor: David François Fischer Lokou, Oberschaeffolsheim (FR)

(73) Assignee: SPINE ARCH BREVET, Oberschaeffolsheim (FR)

( * ) Notice: Subject to any disclaimer, the term of this patent is extended or adjusted under 35 U.S.C. 154(b) by 122 days.

(21) Appl. No.: 15/573,722

(22) PCT Filed: May 11, 2016

(86) PCT No.: PCT/FR2016/051116
§ 371 (c)(1),
(2) Date: Nov. 13, 2017

(87) PCT Pub. No.: WO2016/181078
PCT Pub. Date: Nov. 17, 2016

(65) Prior Publication Data
US 2018/0140341 A1    May 24, 2018

(30) Foreign Application Priority Data
May 11, 2015 (FR) ..................... 15 54199

(51) Int. Cl.
*A61B 17/86* (2006.01)
*A61B 17/72* (2006.01)
(Continued)

(52) U.S. Cl.
CPC ...... *A61B 17/8685* (2013.01); *A61B 17/7208* (2013.01); *A61B 17/869* (2013.01);
(Continued)

(58) Field of Classification Search
CPC . A61B 17/72; A61B 17/7208; A61B 17/7233; A61B 17/7291; A61B 17/84;
(Continued)

(56) References Cited

U.S. PATENT DOCUMENTS 6,514,257 B2 * 2/2003 Dovesi .................. A61F 2/0811
411/438
6,558,386 B1   5/2003 Cragg
(Continued)

FOREIGN PATENT DOCUMENTS

EP    1 265 541 B1    11/2008
EP    1 176 916 B1    7/2013
(Continued)

OTHER PUBLICATIONS

International Search Report (PCT/ISA/210) dated Sep. 23, 2016, by the European Patent Office as the International Searching Authority for International Application No. PCT/FR2016/051116.
(Continued)

*Primary Examiner* — Lynnsy M Summitt
(74) *Attorney, Agent, or Firm* — Buchanan Ingersoll & Rooney PC (57) ABSTRACT

The purpose of the present invention is a new implant for medical use enabling the fixation of at least two adjacent bone elements in a rapid, secure and minimally invasive manner. Said implant is a device in two distinct parts forming a screw once said two parts are assembled. The present invention describes also a fixing method of at least two adjacent bone elements implementing said new implant forming a screw. Said method is particularly adapted for joining at least two vertebrae in order to achieve an arthrodesis; said implant forming a screw is then of a curved shape that makes it particularly well adapted for the spine surgery.

16 Claims, 5 Drawing Sheets

(51) Int. Cl.
*A61F 2/44* (2006.01)
*A61F 2/30* (2006.01)

(52) U.S. Cl.
CPC .. *A61F 2/4465* (2013.01); *A61F 2002/30131* (2013.01); *A61F 2002/30224* (2013.01); *A61F 2002/30289* (2013.01); *A61F 2002/30405* (2013.01); *A61F 2002/30563* (2013.01); *A61F 2002/30622* (2013.01)

(58) Field of Classification Search
CPC ..... A61B 17/842; A61B 17/846; A61B 17/86; A61B 17/8625; A61B 17/863; A61B 17/8635; A61B 17/8685; A61B 17/869; A61B 2017/8655
See application file for complete search history.

(56) References Cited

U.S. PATENT DOCUMENTS

| | | | |
|---|---|---|---|
| 8,343,197 B2* | 1/2013 | Gonzalez-Hernandez | A61B 17/1728 606/286 |
| 8,623,049 B2* | 1/2014 | Ward | A61B 17/0401 606/104 |
| 9,888,918 B2* | 2/2018 | Moskowitz | A61B 17/0642 |
| 2004/0243129 A1* | 12/2004 | Moumene | A61B 17/8625 606/315 |
| 2005/0154390 A1* | 7/2005 | Biedermann | A61B 17/7028 128/898 |
| 2009/0319043 A1 | 12/2009 | Mcdevitt et al. | |
| 2010/0256690 A1* | 10/2010 | Appenzelleir | A61B 17/8057 606/305 |
| 2014/0222088 A1* | 8/2014 | Zwirkoski | A61B 17/846 606/301 |
| 2015/0012048 A1 | 1/2015 | Huebner et al. | |
| 2015/0018886 A1* | 1/2015 | Ali | A61F 2/4455 606/279 |
| 2015/0105830 A1* | 4/2015 | Biedermann | A61B 17/8685 606/317 |
| 2015/0190186 A1* | 7/2015 | Fang | A61B 17/864 606/304 |
| 2015/0257800 A1* | 9/2015 | Harshman | A61B 17/7208 606/62 |

FOREIGN PATENT DOCUMENTS

| | | |
|---|---|---|
| EP | 2 859 856 A1 | 4/2015 |
| FR | 2 2951 370 A1 | 4/2011 |
| WO | WO-2015095353 A1 * | 6/2015 |

OTHER PUBLICATIONS

Written Opinion (PCT/ISA/237) dated Sep. 23, 2016, by the European Patent Office as the International Searching Authority for International Application No. PCT/FR2016/051116.

* cited by examiner

IMPLANT FOR THE FIXATION OF BONE ELEMENTS

The purpose of the present invention is a new implant for medical use enabling the fixation of at least two adjacent bone elements in a rapid, secure and minimally invasive manner. Said implant is a device in two distinct parts forming a screw once said two parts are assembled. The present invention describes also a fixing method of at least two adjacent bone elements implementing said new implant forming a screw. Said method is particularly adapted for joining at least two vertebrae in order to achieve an arthrodesis; said implant forming a screw is then of a curved shape that makes it particularly well adapted for the spine surgery.

With regards to ageing of the population and also to the rhythm of life of the active population, the bone problems generate or are a part of the clinical picture of a lot of pathologies. In addition the traumas related to accidents, shocks and falls, can also generate problems at the bone level requiring a surgical operation. The possibility of fixing bone elements to each other in order to stabilize or to correct a given position is thus an important medical challenge. Indeed, in the field of spine surgery in particular the fact of being able to solidarize bone elements in order to stabilize given areas and/or to release compressed nerve bundles and is often the only way of relieving the patients.

In the field of the orthopaedic surgery one commonly uses plates and screws in order to stabilize adjacent bone areas or to confer to them a given position. The materials used are obviously solid and the material and the equipment impose many mechanical constraints. To allow more adaptation and to authorize more possibilities with the surgeons, different devices were implemented in order to allow a better surgical answer for each patient: surgical screws in combination with different angles, static plates, articulated plates, cages, etc.

In the particular field of spine surgery, surgeons use in general pedicle screws also called tulip screws to solidarize vertebrae. These screws of medical use are straight screws that allow arthrodesis, that is to say the bone fusion between at least two vertebrae. This technique is commonly used for fractures, scoliosis, instability and significant pain. Even if this technique is very usually practised, the installation of pedicle screws remains a difficult procedure that is reserved to the specialized surgeons and is likely to involve false ways. In the cases of false ways, one or more screws are not correctly placed, they can wound the nerve rots or have a solidity defect. To address this possibility of false way, several sophisticated systems of assistance to guidance are used by the surgeons, one will in particular quote «the navigation» including infrared detection coupled to a per operative scanner. These navigation systems allow decreasing the risk of error of trajectory. However the error risk factor remains important because the arthrodesis practised to date require at least four pedicle screws and more often six to eight pedicle screws.

In the prior art, several documents describe the fixation of two adjacent bone elements by more or less complex and more or less invasive systems implementing metal elements and sometimes elements being able to adopt a curved shape. If we are interested more particularly in the fixation of vertebrae the patent EP1176916 describes as an example a system of spine fixation including a linking element that can be arched of which the length is established so that it extends between two adjacent vertebrae without protrusion on the vertebrae. This linking element that is not obligatory rigid, nor obligatory arched, allows the fusion and/or the stabilization of vertebrae. The implantation of several of these elements inside one or several bores practised in vertebral bodies is also considered. According to EP1176916 the linking elements are made of metal, bone, morphogenic protein, carbon fibre composite, nitinol, biodegradable material or a combination of these materials. An opening of insertion is practised in each adjacent vertebral body and calculated so that the exit openings coincide in the intervertebral space of the two adjacent vertebrae to fasten. The installation of this linking element in its arched version requires the realization of several drillings according to distinct and very precise approach what is complex to realize in situ and risk factor for the patient in an operation area with difficult approach and that is very innervated.

One will also cite the patent EP1265541 that describes the use of an axial spinal implant intended to be inserted in a curved bore practised at the caudal level through the sacrum and extending in the cephalad direction through at least two vertebral bodies. The bore is practised in order to be able to insert axial lengthened implants in the alignment with a visualized trans-sacral instrumentation/fusion line (TASIF) from the caudal level towards the head of the patient. The bore and the implant present a curve to comply with the spine morphology of the patient in its sacred-lumbar area. This method is invasive because if an upper stage is targeted it is nevertheless necessary to realize a caudal bore in order to reach the area to be implanted. The implant presents moreover at least a threading in order to come in catch with the bone of the crossed vertebral body to maintain the implant in position and to avoid a caudal retraction of the axial spinal implant. This method is usually used for the spine surgery but does not allow considering the installation of an implant that is not axial. Moreover it is invasive and requires a sophisticated imaging equipment to minimize the risks at the time of the bore realization which is obligatory partly caudal through the sacrum, and of the insertion of the axial implant.

One will also cite EP2859856 that describes the use of a bone screw made up by two distinct elements conferring it a limited longitudinal flexibility. It consists of a rod equipped with a groove in which a helical element is beforehand inserted. The groove is designed so that this helical element is suited to substantially slip upwards or downwards into the longitudinal axis of the screw once the latter is in place; thus according to the mechanical constraints imposed on the screw, it will be able somewhat to adapt itself to the constraints of its environment. However this screw is straight. It is intended to be inserted in a bone and potentially a vertebra in a pedicle approach. Because of its longitudinal flexibility it is inapt to fix two bone elements with each other. Moreover the two elements of this type of screw must be assembled before their use in patients.

Finally the patent FR2951370 as an example describes an implant that allows an instrumented stabilization of the spine using an articulated cage that comes to fill the intersomatic space. This is a method making it possible to replace a damaged intervertebral disc and to fuse two adjacent vertebrae. Said cage is maintained in the desired position by pedicle screws. However it is well-known from the prior art that the installation of the cage and the screws, which are relatively numerous, requires a control by imaging of the implantation area and especially a great experience and a specific control from the neurosurgeon who will have to avoid any "false way" when installing each pedicle screw in order not to injure the area to be implanted. This technique and this type of implants are usually used but the technique of installation of this kind of implants presents in particular the disadvantages related to the positioning of the pedicle screw described above and impose the use of a complex and expensive imaging material.

Thus the techniques used to date present several disadvantages including the complexity of the devices to implant, the transpedicle approach for the fixation screws of these devices that is relatively invasive and generator of side-effects (haemorrhage, nerve injury, etc.), the need for an follow-up implying powerful imaging techniques, all of which being risk factors, involving technicality and costs that are to be taken into account.

The presence of nerves, blood vessels and other tissues that must necessarily be preserved at the time of bone surgeries impose limited access ways and approaches to the surgeon. The errors of trajectories are all the more numerous as the access ways are difficult or exiguous. In certain cases taking into account the spatial configuration of the bone elements to solidarize the techniques known from the prior art do not offer any solution. Thus there is a real need for new technical solutions opening new possibilities of fixation of bone elements in specific configurations.

The curved screw is one of these solutions, however it was never proposed to date. As a matter of fact, the screw has the advantage of allowing the installation of a solid fixation requiring only one access way. The curved shape allows as for it to work with access ways offering working angles that are not appropriate for the straight screws known from the prior art.

The present invention proposes a simple surgical implant that allows to realize the fixation of at least two adjacent bone elements, for example two adjacent vertebrae, with no risk of false way, with no particular technical difficulty and without expensive technical help other than a simple X-ray equipment.

In the case of the spine surgery, contrarily to the technique implementing pedicle screws, the implants according to the present invention are not positioned in the vertebral pedicles but allow to solidarize directly the vertebral bodies between them. The device is from the start more solid than the pedicle screws commonly used in the prior art. Furthermore the vertebral bodies being large, in the range of 4×5×3 cm, the risk of an extracorporeal way is very limited compared to the vertebral pedicles that are in the rage of 1×0.8 cm and are quite difficult to identify even with efficient imaging techniques.

The present invention thus proposes also a new method for the fixation of at least two adjacent bone elements, as an instance two adjacent vertebrae, with no risk of false way and with no particular technical difficulty for the surgeon. This method allows also a considerable time gain in the case of the stabilization of more than two adjacent bone elements such as several vertebral levels. Moreover this new surgical implant which once set up forms a screw, is placed directly in the bone element, with no staple nor nail, thus an arthrodesis operation as en example can be realized with a closed spine between the nerve bundles and without damaging the nerves.

In the present invention, the following terms are used to describe the new surgical implant, the new method for fixation implementing it and the elements constituting it. They are used in both the plural as in the singular.

By «patient» is meant a human being or an animal whose symptoms or pathology require the intervention of a surgeon in order to solidarize at least two bone elements between them. For example a patient is an individual having undergone a fracture of vertebra or presenting a scoliosis, a vertebral compressing etc. the proposed method in order to alleviate pain of said patient being the realization of an arthrodesis, that is to say the bone fusion between two vertebrae.

By «bone element» is meant anatomical bone elements requiring a surgical intervention of stabilization or reparation but also any implant that replaces for all or part an anatomical bone element with an implant made of metal or metal alloy, ceramic, polymers, or any other biocompatible material.

By «curve» is meant a shape describing a plane arc or in three dimensions and not necessarily regular.

By «rod» is meant a solid element of a cylindrical shape, filled or hollow, that constitutes the first element of the implant according to the invention, that includes on whole or part of its length an element of guidance in the shape of a helical groove intended to receive the helical element. The rod can be of a straight shape, curved or combined; when combined the rod presents a straight part and a curved part without the stem presenting obligatorily a symmetry.

By «helical element» is meant a filled solid element of a helical shape, that can be flexible, aimed at being inserted along a rod in order to form a screw with said rod constituting in particular the threading of the screw thus formed. This helical element will include at least one core and according to the embodiment a thread, said thread constituting the thread of the implant forming a screw.

By «screw» is meant a cylindrical or conical rod, made of a solid matter that can be flexible, and presenting a helical relief or a threaded part serving to exert a pressure, in particular to realize an assembly.

By «separate thread» one mean a thread that is aimed to form a screw with a rod once in the desired position but that is not integral with said rod before being in the desired position.

By «helical groove» is meant a helical groove practised on the whole or part of the external face of the rod, and whose shape allows the passage and the support in its centre of the core of the helical element, core whose shape is chosen according to that of the groove. For example in cross section the groove has a C shape, whose opening is oriented towards the external surface of the rod, thus of closed profile, what prevents the exit of the core of the helical element. According to another embodiment in cross section the groove has a flared up shape, a "V" for example.

By «helical move» is meant a move consisting of a rotational component and a translational component. In the case where the helix pitch of the helical element desired is wide enough, the helical movement actuation can be obtained by a simple push in translation. On the contrary in the case where the helix pitch of the desired helical element is narrow enough the helical movement actuation can be obtained by instigating a simple rotation to the considered element.

By «portion» is meant a part of a slightly cylindrical shape of the rod.

The invention is directed to a surgical implant for the fixation of at least two adjacent bone elements of a patient, characterized in that it is composed of a rod being intended to be firstly inserted in a bore practised in the at least two bone elements and at least one distinct helical element being intended to be inserted secondly on said rod, the unit when set up forming a screw.

The surgical implant according to the invention is particularly adapted when said bone elements are vertebrae.

In a preferred and elaborate embodiment of the invention the surgical implant includes in addition performed on the external surface of the rod, as many guiding elements in the shape of helical grooves than of helical elements, said guiding elements in the shape of helical groove each presenting an opening on whole or part of their length in the direction of the bone element, and each of said helical element includes a core having a shape and dimensions complementary to the shape and dimensions of at least one guiding element in the shape of a helical groove in order to be able to be inserted and to slide in said groove and an anchoring element present on whole or part of the core length and protruding through the opening in direction of the bone element.

Said helical groove can be more or less narrow. Thus in one embodiment of the invention this groove can be very opened and appear in the shape of a slight undulation at the surface of the rod, undulation in which the part forming the core of the helical element is going to be guided and come to fit, the non inserted part coming in contact of the bone elements and wedge the helical element between the bottom of the groove and the bone element thereby ensuring the anchor of the screw. In this embodiment the helical element is ideally in section of a cylindrical shape, ovoid, or any other geometrical shape authorizing its sliding within the groove.

In a preferred embodiment of the invention presenting a groove, at least one of the anchoring elements is a thread. Said thread can be realized according to several profiles, in particular rounded or slicing according to whether one searches an anchoring by support on the bone element or by insertion in this one.

According to a specific embodiment presenting a groove, the at least one thread is not of a constant height on its whole length. Thus the thread height emerging from the opening can be variable. An important height allowing to ensure an anchoring in a more crumbly bone element and a less important height allowing an anchoring in a harder bone tissue. The invention can also be realized with no thread on certain parts of the helical element in particular those which will be surrounded by an area of non-bone tissues once the implant is set up. According to another additional characteristic the thread present on its walls elements such as lamellas or pins, eventually sectile, aiming at anchoring said thread in the bone with no possibility of return unless being constrained to do so by a movement exerted by the surgeon with the necessary frame to fold them or break them.

In the embodiments presenting a groove, the groove is not necessarily practised on the whole length of the rod. It can in particular be envisaged not to practise a groove on the part of the rod that will occupy the most deep part of the boring, that is to say located opposite to the opening practised by the surgeon to realize the boring and to insert the implant. According to an embodiment of the invention the depth of the at least one helical groove is not constant on its whole length. It can thus be considered to practise grooves of variable depths by decreasing the depth of the groove for the parts of the screw that, once this one is set up, will be located in the bone elements and by increasing the depth of the groove for the parts of the screw going through non-bone tissues. This last configuration allowing to have the thread protruding from the groove in a more or less important manner according to the parts of the rod.

In a variation of the invention several parallel grooves are practised on the rod to receive as many helical elements so as to form, once the elements are set up, a screw with several threads. In the embodiments of the invention presenting at least one groove, the core of the helical element present in cross section perpendicular to the longitudinal axis of this core a shape, for example in V, in U or round, complementary to the guidance element with shape of a helical groove for example with a widened shape in V, straight in U or slightly closed in C. The core of the helical element being adjusted in order to allow its sliding within the said groove, while forcing said sliding, that is to say while preventing that the core of the helical element adopts another conformation than the one mechanically imposed by the groove and by the setting tool instigating it a helical movement. It must be noted that the pressure of the bone element on the anchoring element of the helical element maintains this last in the guidance element with the shape of a groove. In a preferred embodiment the helical groove present a profile of a widened shape with the opening directed in the direction of the bone element to assemble. The core of the helical element with a complementary shape will come to fit in the groove during the installation by the surgeon and will be maintained in place by the mechanical constraints imposed by the shape of the groove, the thread coming to fit in the bone and the pressure exerted by the setting tool.

For a better hold of the implant according to the invention it could however be required to improve this support, in particular if the bone element is weakened by places. According to an alternative characteristic the helical groove present a C shaped profile with an opening directed in the direction of the bone element to assemble. Of course any other similar closed profile will ensure the same function of resistance of the core of the guidance element and presents an alternative of the invention. The profile of the at least one helical groove will be considered as closed if in cross section perpendicular to the longitudinal axis of said at least one groove, the dimension of the opening of the at least one groove is lower to the greatest dimension of the core of the at least one helical element measured according to any straight line parallel with the abovementioned opening.

The shape of the rod determines the shape of the implant, thus in a particular embodiment the rod is slightly straight and the surgical implant forming a screw is slightly straight; in a preferred embodiment the rod is curved and the surgical implant forming a screw when set up is also curved. In a specific embodiment the rod is curved in various plans. According to an additional characteristic the shape of the surgical implant forming a screw according to the invention is curved. According to another additional characteristic the shape of the surgical implant is mixed, that is to say it presents one or more straight portion and one or more curved portion.

The materials used for the realization of the surgical implant according to the invention are biocompatible solid materials for example of the type metal or metal alloy, particularly titanium or titanium-based alloys and/or steel or the steel-based alloys, ceramics of medical use, polymeric materials of medical use, said materials being considered alone or in combination. According to an additional characteristic the rod and the helical element are made of metal or in a metal-based alloy. In a particular embodiment, the mechanical properties of the rod and the distinct helical element being different, these two elements are realized in different biocompatible materials; typically metals or metal-based alloys having different properties such as flexibility, elasticity, hardness, stretching, and dilatation. In another distinct embodiment the rod itself is realized in different biocompatible materials in order to present according to its sections different properties, in particular flexibility. Of course in specific embodiments it can be considered different surface treatments of the rod, of the core of the helical element or of the thread of the latter in order for example to ensure the biocompatibility, the cutting-edge, the spring effect, the sliding or on the contrary the adherence of such or such of these elements. In a specific embodiment the helical element is realized in materials having an elasticity such as for instance the stainless steel.

When the rod is realized in a rigid material, the surgeon must practise a boring within the bone elements to assemble whose curve is identical to that of the rod. When the rod is realized in a solid but flexible material, the rod is likely to adapt to any curve of the boring carried out by the surgeon according to predetermined parameters. Thus according to an additional characteristic the rod is realized in one or more biocompatible flexible materials.

The simplicity of this surgical implant makes it particularly suitable to the morphology of the adjacent bone elements to be assembled. Indeed it is easy to manufacture «customised» surgical implants forming a screw having a shape that is slightly straight or curved, presenting a symmetry or not with respect to said curve, etc. All the shapes are authorized in the present invention according to the area to be implanted. For an implantation at the vertebral level, one will privilege for example a surgical implant of a curved shape in order to adapt to the vertebrae morphology and to their articulation. The curve is then determined according to the morphology of the bone elements to solidarize. The curve of the implant according to the invention will not necessarily be plane and will be able to present twists. The curve of the implant according to the invention is not necessarily regular. When it is regular and in the absence of a twist, a curved part of the implant according to the invention will describe an arc typically ranging between 1 and 180 degrees, preferentially between 15 and 90 degrees, more preferentially between 30 and 60 degrees.

Generally whatever the shape of the implant according to the invention is it could be considered to realize only certain parts of the rod in a flexible material. For example the flexible parts could be intended so as to be positioned outside the bone elements to assemble, for example two vertebrae, so as to form a kind of hinge and to preserve a certain flexibility of the implant.

According to a specific embodiment, the implant according to the invention present a distinct blocking device of the helical element in a desired position the rod. This blocking can be carried out by any mechanical mean known by one skilled in the art, in particular by the insertion of a nail, a pin or a staple crossing the elements to be immobilized, of a sleeve or a nut enclosing them or a spacer thread or a wedge making brake between the bottom of the groove and the guidance element. One skilled in the art will be able to also obtain this blocking by using adhesives, resins, magnets or cements and any other biocompatible mode of fixation.

According to a specific embodiment, the implant according to the invention presents a hooking device allowing the installation and the withdrawal of the rod and the helical element by the surgeon using an adapted ancillary. This hooking device is according to a preferred embodiment, located on a part of the rod not inserted in the bone elements. According to a preferred characteristic the hooking device is located on a part of the end of the helical element not inserted in the bone element. The hooking device can consist of any means known by one skilled in the art, such as for example a threading, a hook, a ring, a notch, a flat, a magnet, a relief, a print, a withdrawal, a boring.

The invention also propose a method of fixation of at least two bone elements, implementing the surgical implant consisting of a rod and at least one distinct helical element, consisting in:

to practise using a boring tool a bore presenting the characteristics defined by the surgeon according to the bone elements to solidarize, then to insert the rod in the bore thus practised using an installation tool, then to insert each of the at least one distinct helical element on said rod using an installation tool allowing to instigate separately or simultaneously the different components of the helical movement to said at least one helical element.

In the embodiments of the invention presenting a guidance groove the method is identical to that which has just been described, being specified that the insertion of each of the at least one distinct helical element on said rod is done at the level of the guidance element in the shape of a helical groove and can moreover comprise an additional final step consisting in blocking each of the at least one helical element on the rod in the desired position using a blocking device. The withdrawal of the surgical implant according to the invention will be made while proceeding to the same operations than the installation but in the inverse order.

It will be understood easily that the rod of the implant according to the invention can be inserted like a nail by simple percussion or any other push on its external end, what can be done without to instigate to it any rotation movement. The rod of the implant according to the invention can even be inserted in a bore or a housing presenting a certain curve, which is rigorously impossible for a traditional rigid screw. If the bore presents a constant radius of curvature and being in only one plan, that is to say without twist, the rod of the implant according to the invention could be rigid but must also have the same radius of curvature as the abovementioned bore. If the radius of curvature of the bore is not constant or if it presents one or more twists the rod of the surgical implant according to the invention must necessarily have certain flexibility.

One will also understand easily that the flexibility and/or elasticity of the distinct helical element according to the invention allow its insertion by a simple screwing along the rod, even curved, by instigating to it a helical movement. In the embodiments of the invention presenting a groove, the insertion of each of the at least one distinct helical element on said rod at the level of the guidance element in the shape of a helical groove allow a very precise installation.

The characteristics of the invention abovementioned, as well as others, will more clearly appear on reading the following description of an example of realization, said description referring to the attached figures, among which.

Theses FIGS. 1 to 6 show an example of implementation of an implant according to the invention and describe the solidarization of two adjacent vertebrae by means of a surgical implant (1) such as described above. The illustrated embodiment makes appear a rod (2) of a curved shape and a helical element (3) that is inserted in a guidance element in the shape of a helical groove (4).

This rod according to FIGS. 7 to 14 presents on one end a head in a conical shape able to penetrate the bone and on the other end a part aimed at being fixed on the installation tool. The size of this head is typically of 6 mm between its base and its end. The developed length of the rod is of 70 mm and its diameter of 4 mm measured from the bottom of the groove to the bottom of the groove and of 6 mm in outcrop of groove. The curvature arc of the rod fits in a circle with a radius of 90 mm, and describes an angle of 44.6°.

Figure 1:
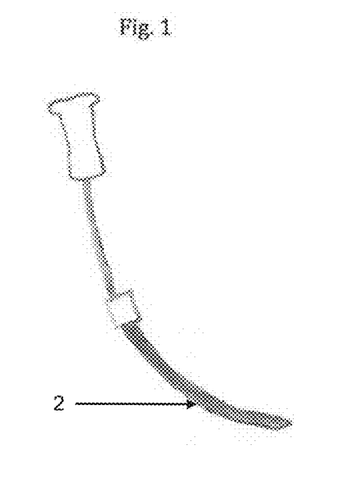
FIG. 1 represents a view of the rod (2) constituting the part of the surgical implant (1) that is firstly inserted in the operation area.
Figure 2:
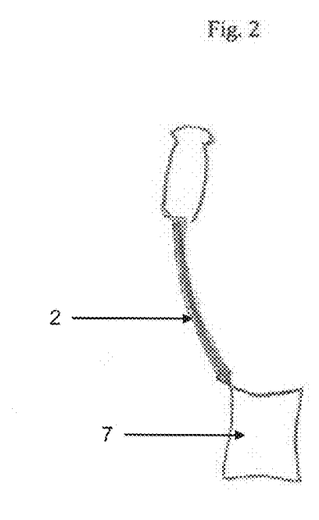
FIG. 2 represents a view of the rod (2) constituting one of the two parts of the surgical implant (1) at the time it will be inserted in a vertebra using a tool for boring and installation.

FIGS. 1 and 2 illustrate the first element constituting the surgical implant (1) according to the invention, that is to say the rod (2) and an adapted installation tool. This first element is inserted using a boring and installation tool within two adjacent bone elements, here two vertebrae. This first step is represented in FIG. 2.

Figure 3:
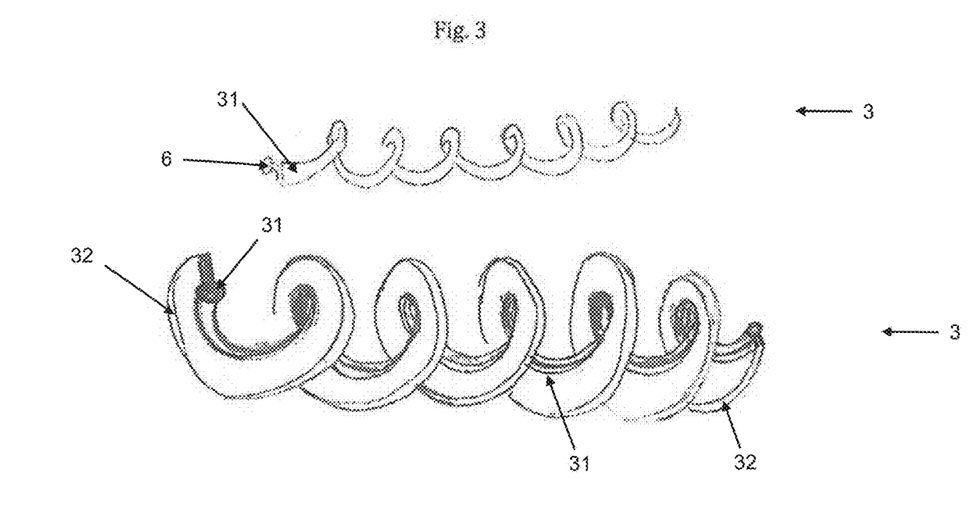
FIG. 3 represents a view of the helical element (3) in a classic embodiment and in a particular embodiment that makes a thread (32) appear on the part of the helical element (3) in contact with the bone element and a core (31) on the internal part of the helical element (3)

FIG. 3 shows the detail of the second element constituting the surgical implant (1) according to the invention, the at least one distinct helical element (3). The first scheme shows the core (31) of this helical element (3) that will come to slide in the guidance element in the shape of a helical groove (4) of the rod (2), and a hooking device (6). The second scheme shows the helical element (3) consisting of a core (31) and a thread (32) that is formed with the core (31). In a preferred embodiment the helical element presents a distal end that will come in outcrop or in abutment against the base of the head in a conical shape on the distal end of the rod and a proximal end equipped with a fixation device for the installation tool. Typically the external diameter of the helical element is of 10 mm and the internal diameter is of 4 mm.

Figure 4:
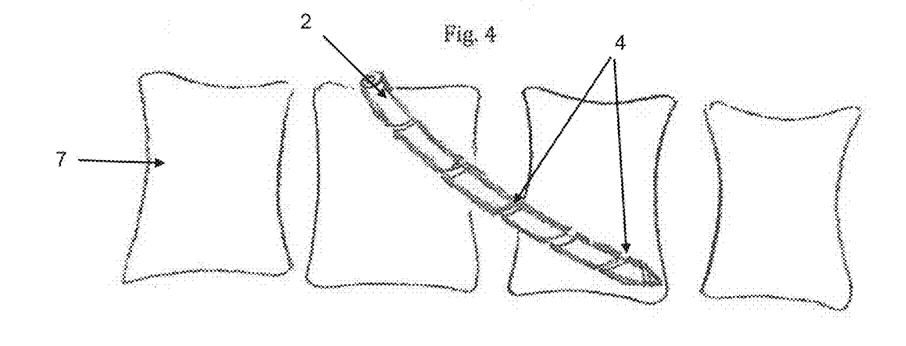
FIG. 4 represents the first part of the surgical implant (1) according to the invention, that is to say the rod (2) once inserted between two vertebrae, one sees a guidance element in the shape of a helical groove (4) practised on the external surface of the rod (2)

FIG. 4 shows the rod (2) once positioned within two vertebral bodies to solidarize. This rod (2) presents a guidance element in the shape of a helical groove (4) aimed at receiving the core (31) of the helical element (3) that is sized to be complementary to the guidance element in the shape of a helical groove (4). The further step is the installation of the helical element (3) using an installation tool instigating it an helical movement allowing its insertion around the rod (2).

Figure 5:
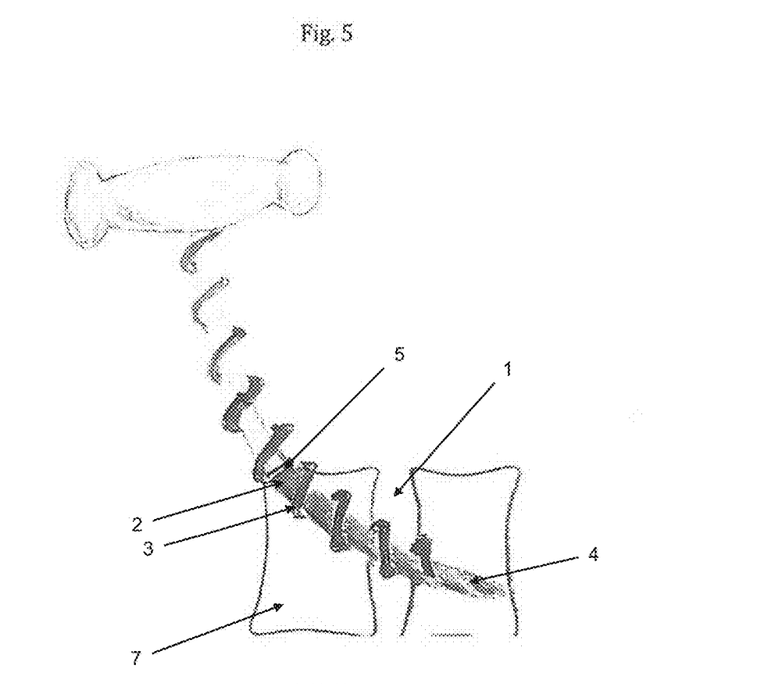
FIG. 5 represents the insertion of the second part of the surgical implant (1) at the level of two adjacent vertebrae, one distinguishes there the rod (2) and the helical element (3) that slides along said rod (2) within the vertebral body thanks to an adequate installation tool.

FIG. 5 shows the abovementioned step of introduction of the helical element (3) on the rod (2) within the guidance element in the shape of a helical groove (4) ; said rod (2) serving as a guide.

Figure 6:
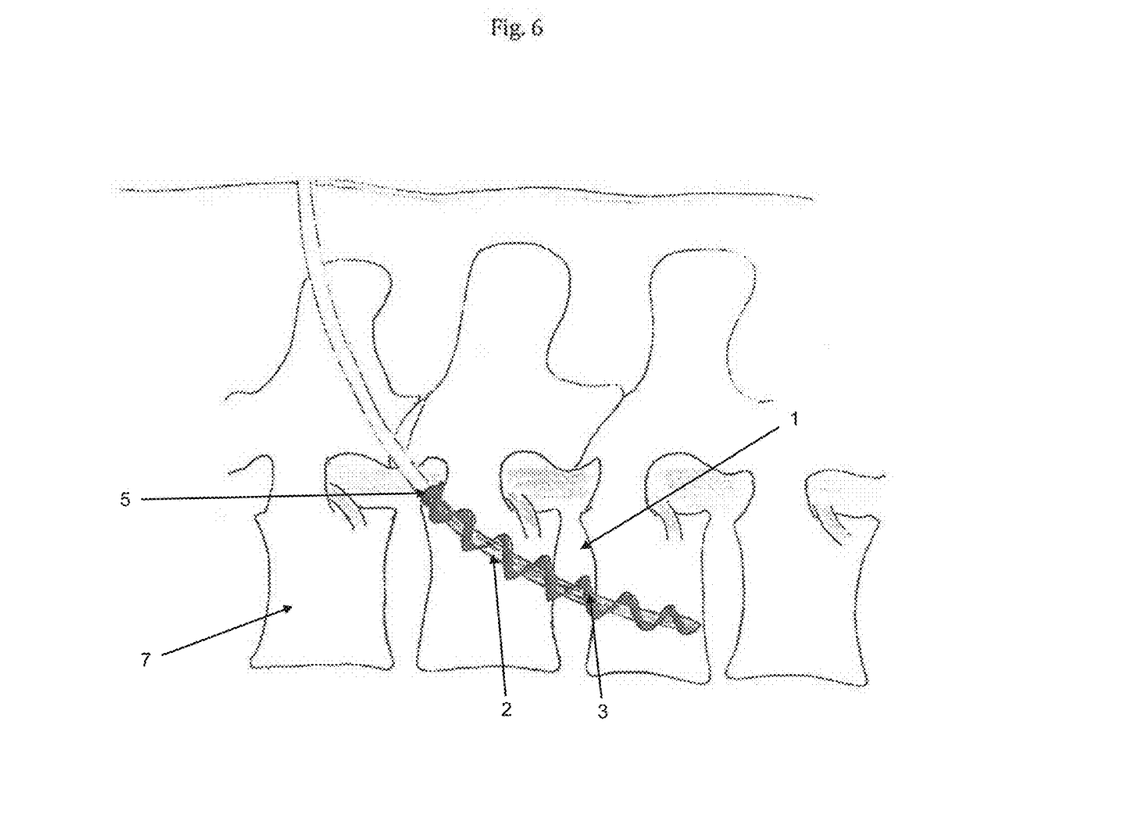
FIG. 6 represents the surgical implant (1) once positioned between two adjacent vertebrae, one sees the rod (2) and the helical element (3) in their final position, thus forming a screw within two adjacent vertebral bodies.

FIG. 6 shows the surgical implant (1) in its final position within the two vertebral bodies in our example. The helical element (3) is inserted along the rod (2) and blocked in its final position by a blocking device (5). The pedicles of the vertebrae are not affected by the installation of the surgical implant (1) thus avoiding any problem of false way and/or nervous or vascular injury.

In a particular embodiment, the present invention concerns a curved surgical implant (1) for the fixation of at least two adjacent bone elements of a patient, which is composed of a rod (2) being intended to be inserted firstly in a boring practised in the at least two adjacent bone elements, and of at least one distinct helical element (3) aimed at being inserted secondly on said rod (2), the assembly when set up forming a screw.

In a second particular embodiment, the present invention concerns a curved surgical implant (10) for the fixation of at least two adjacent bone elements of a patient, which is composed of a rod (2) being intended to be inserted firstly in a boring practised in the at least two adjacent bone elements, and of two distinct helical elements (3) being intended to be inserted secondly on said rod (2), the assembly when set up forming a screw.

In a preferred embodiment said surgical curved implant (1) is composed of a rod (2) being intended to be inserted firstly in a boring practised in the at least two bone elements and of at least one distinct helical element (3) being intended to be inserted secondly, and:

said rod (2) comprises practised on its external surface, as many guidance elements in the shape of a helical groove (4) as of helical elements (3), said guidance elements in a helical shape (4) presenting each a, opening in direction of the bone element, and each of the at least one distinct helical element (3) includes a core (31) having a shape and sizes complementary to the shape ad sizes of at least one guidance element in the shape of a helical groove (4) in order to be able to fit and slide within said at least one guidance element in the shape of a helical groove (4) and one element present on the whole or part of the core (31) length and protruding by the opening in the direction of the bone element, the assembly when set up forming a screw.

The installation of such an surgical implant (1) according to the invention is typically realized using two distinct tools aimed at position very precisely the two element constituting said surgical implant (1), that is to say the rod (2) and the at least one distinct helical element (3) within the guidance element in the shape of a helical groove (4). A boring tool allows to practise a boring in the two bone elements to solidarize according to a way determined by the surgeon. Then a first tool allows the installation of the rod (2), and then a second installation tool allows the insertion of the at least one helical element (3) around the rod within the guidance element in the shape of a helical groove (4) by instigating it a helical movement. The rod (2) installed beforehand serves as a guide for the at least one helical element (3). According to an additional characteristic a blocking element can be envisaged in order to determine very precisely when the at least one helical element (3) is in its final position. Said blocking element can be located either at the distal end of the rod (2), or at its proximal end that is to say at the level of the insertion point of the rod (2) in the first bone element. This blocking element can also have a function of blocking device (5) when it is located in proximal position of the surgical implant (1) once installed.

When the surgeon evaluates that it is applicable according to the bone elements to assemble and to the material constituting the rod (2), it can be planned to use a tool for boring and installation that uses the rod (2) of the surgical implant (1) presenting a sharpened distal end as a boring head. In this embodiment there is no prior boring step when the method according to the invention is implemented.

According to an additional characteristic the surgical implant (1) presents a hooking device (6) in order for the surgeon to ensure easily its installation and its withdrawal. This hooking point (6) is ideally located at the level of the proximal end of the surgical implant (1) that is to say at the level of the insertion point of the rod (2) in the first bone element. The withdrawal of the surgical implant (1) or removal is made while proceeding to the same operations that the installation but in the inverse order.

In a preferred embodiment the curved surgical implant (1) present a rod (2) and at east one distinct helical element (3) aimed at being inserted on said rod (2) forming thus a screw having a developed length of between 17.5 mm and 280 mm, preferentially 35 mm and 140 mm, more preferentially between 50 mm and 90 mm, and fitting in an arc ranging between 1 and 180 degrees, preferentially between 15 and 90 degrees, more preferentially between 30 and 60 degrees.

In order to provide more solidity to the implant it can be envisaged embossed elements such as pins, on the walls of the thread (32) f the at least one helical element (3) oriented in an appropriate manner in order to oppose a resistance to the unscrewing of the rod (2) and the helical element (3) forming a screw when set up by the surgeon.

In a preferred embodiment the invention concerns a surgical implant (1) for the fixation of at least two adjacent vertebrae of a patient, that is composed of a curved rod (2) being intended to be inserted firstly in a boring presenting the same curve practised in the at least two vertebrae and of a distinct helical element (3) being intended to be inserted secondly, and that:
said rod (2) comprises practised on its external surface, as many guidance elements in the shape of a helical groove (4) as of helical elements (3), said guidance elements in a helical shape (4) presenting each a, opening in direction of the vertebrae, and
each of the helical element (3) include a core (31) having a shape and sizes complementary to the shape ad sizes of at least one guidance element in the shape of a helical groove (4) in order to be able to fit and slide within said at least one guidance element in the shape of a helical groove (4) and one element present on the whole or part of the core (31) length and protruding by the opening in the direction of the vertebrae,
the assembly when set up forming a curved screw.

In a particular embodiment the surgical implant (1) that once set up if forming a curved screw is intended for the spine surgery and describes an arc ranging between 30 and 60 degrees, preferentially between 40 and 50 degrees for a developed length of the implant (10) ranging between 35 mm and 140 mm.

In an embodiment of the invention, the at least one anchoring element in the shape of a thread (32) protrudes out of the guidance element in the shape of a helical groove (4) in which it is inserted on a height in direction of the bone element typically ranging between ½ and ½₀ of the diameter of the rod (2). In another particular embodiment the thread (32) is not continuous or is not realized on the whole length of the core (31). In another embodiment of the invention the depth of the guidance element in the shape of a helical groove (4) is not constant and presents portions where it is superior to the size of the core (31) fitting in this depth in order to allow the modulation of the height of the thread (32) protruding from the guidance element in the shape of a helical groove (4) so that this one is important in the portions of the implant (1) that are located in a bone element and less important or absent for the portions of the implant which go through non bone tissues.

In a particular embodiment of the invention several guidance elements in the shape of helical grooves (4) parallel with each other are practised on the external surface of the rod (2). Such a realization allow to adopt an important helical pitch facilitating the sliding of the core (31) of the at least one helical element (3) in said guidance elements in the shape of helical grooves (4) while preserving the total length of the anchoring element (32).

The present invention is also directed to a method for the fixation of at least two adjacent vertebrae that implement a surgical implant (1, 10) such as described above, composed of rod (2, 11) and of at least one distinct helical element (3, 12), said method consisting in:
To practise a boring having the characteristics previously defined by the surgeon in function of the vertebrae to solidarize using a boring tool, then
To insert the rod (2, 11) in the boring thus practised using an installation tool under medical radioscopy, then
To insert each of the at least one distinct helical element (3, 12) on said rod (2, 11) using an installation tool allowing to instigate separately or simultaneously the different components of helical movement to said at least one helical element (3), and optionally
To block the helical element (3, 12) on the rod (2, 11) in the desired position using a blocking device (5).

According to an addition characteristic the blocking in final position is realized thanks to a blocking device (5) and/or an abutment element that is placed either in distal position, or in proximal position of the surgical implant (1). According to a particular embodiment the surgical implant presents a blocking device (5) of the distinct helical element (3) in a desired position on the rod (2). The blocking device (5) avoids to the two elements of the surgical implant (1) to move one compared to the other. According to an additional characteristic the blocking device (5) is located in proximal position of the implant (1) and consists in a blocking ring realized in a biocompatible material.

This method if particularly adapted to the fixation of several adjacent vertebrae in a patient presenting a lumber problem requiring the intervention of a surgeon because it allows to avoid the insertion of pedicle screws according to the techniques currently used, what is less invasive and limits largely the side effects linked to the operation of vertebrae fixation. Moreover, the operation can be considered with a closed spine under radioscopy control, while passing between the nerve bundles and without injuring the nerves.

In the case of the spine implantation of an adult patient, the surgical implant (1, 10) according to the invention is of a curved shape describing an arc ranging between 30 and 60 degrees, preferentially between 40 and 50 degrees for a developed length of the implant (1, 10) ranging between 35 mm and 140 mm. As a first step the boring is realized with a first boring tool. Then an installation tool is used in order to place the rod (2, 11) from the cortical layer through the tender part of the first vertebral body and finally towards the second vertebral body to fix. In a second step the at least one distinct helical element (3, 12) is inserted along the rod (2, 11) using an adapted ancillary instrument allowing its insertion by instigating it an helical movement, the rod (2, 11) beforehand positioned in the boring serving as a guide; it is more precisely the core (31, 17) of the at least one helical element (3, 12) that comes to slide within the at least one guidance element in the shape of an helical groove (4, 13). The core (31, 17) of the at least one helical element (3, 12) is inserted until reaching a final position in which it will be blocked by a blocking device (5) located in the proximal part of the implant (1).

Typically for an adult patient, the rod (2) has a diameter of 6.0 mm and the thread (32) of the distinct helical element (3) occupies a space of 2.0 mm on both sides of the rod (2). The assembly of the surgical implant (1) requires thus a boring of around 10.0 mm of diameter in total within the two adjacent vertebrae to fix for an adult patient.

In a particular embodiment the surgical implant (1, 10) presents a developed length ranging between 35 mm and 140 mm and fits in a circle arc ranging between 15 degrees and 90 degrees.

The present invention is also directed to kits containing the material required for the implementation of the method described above, that is to say a surgical implant (1, 10) in one of the embodiments detailed above, un boring tool, an installation tool for the rod (2, 11) and an installation tool for the helical element (3, 12) allowing its insertion by instigating an helical movement; said three tools forming a kit of ancillary instruments.

In a preferred embodiment the kit includes a surgical implant (1, 10) in a curved shape and a kit of ancillary instruments.

EXAMPLE 1

Surgical Implant for the Fixation of Vertebrae

The present example described a surgical implant according to the invention that is perfectly adapted for the solidarization of two vertebrae in an adult patient.

Figure 7:
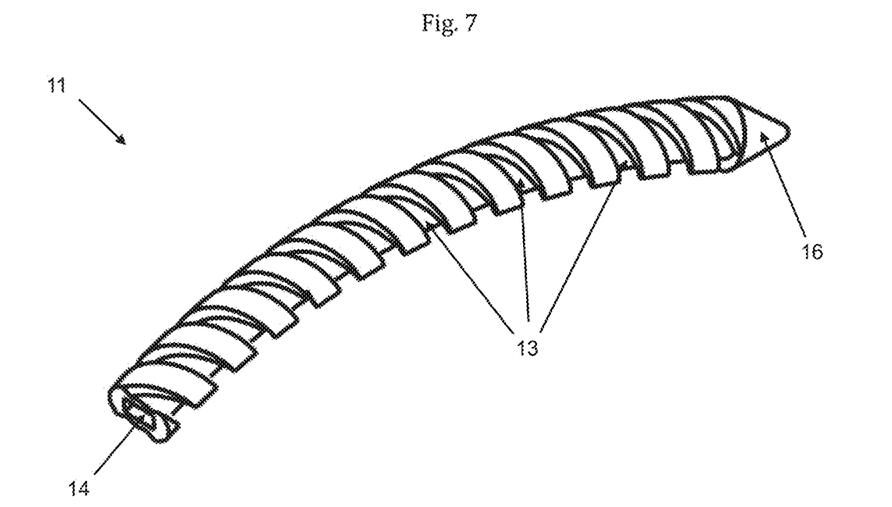
FIG. 7 represents an isometric view of the rod (11) with a double groove (13) of the curved implant (10) from FIG. 12.
Figure 8:
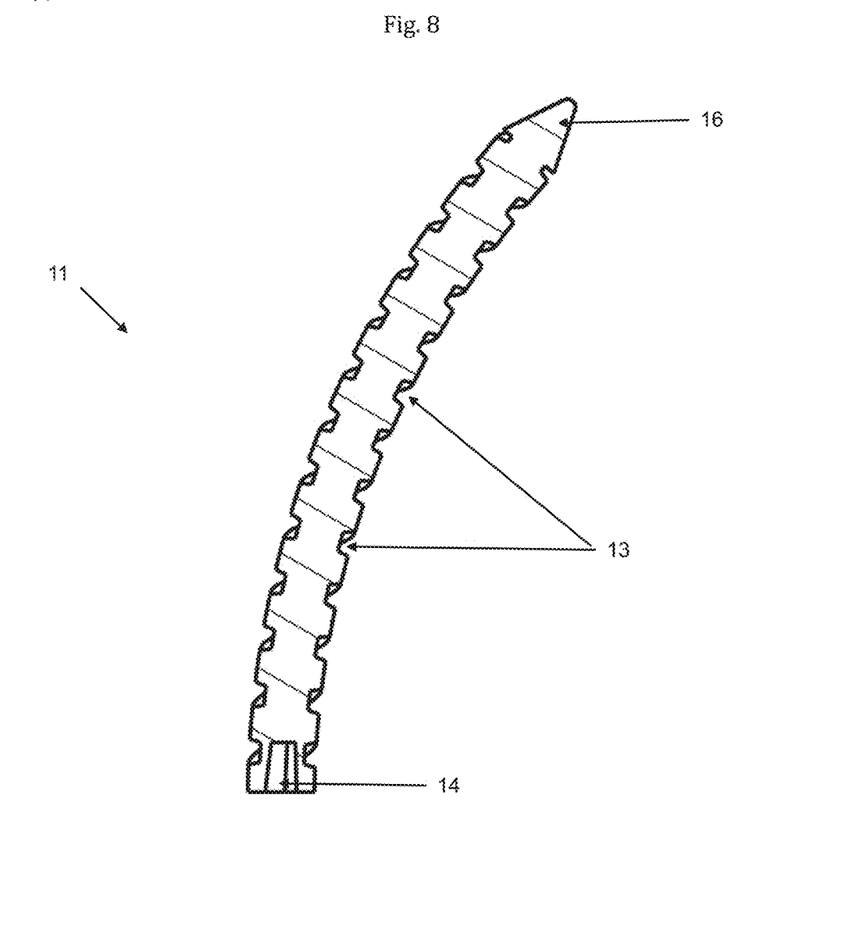
FIG. 8 represents a view in longitudinal section of the rod (11) with a double groove (13) of the curved implant (10) from FIG. 12.

The rod (11) represented on FIG. 7 is of a curved shape in a plan, with a developed length of 70 mm describing an arc of 44.6° and of 90 mm radius. The rod (11) has a diameter of 6 mm and presents two helical grooves (13) that are identical and equidistant on its external surface, said groove having a depth of 1 mm. The proximal end of the rod (11) is equipped with an anchoring or hooking system (14) for the installation tool. Its distal end is equipped with a head in a conical shape aimed at helping the penetration of the rod in the boring beforehand realized by the surgeon in the vertebrae to solidarize. The helical groove (13) presents a flared profile as it is illustrated in FIG. 8 that presents a longitudinal section of the rod (11) making clearly appear the flared profile of the groove (13) whose walls form an angle of 30° one compared to the other. The distance between the higher ends of the walls is of 2 mm. This groove (13) extends until the base of the conical head (16). The head (16) has a length of 6 mm between its end and its base that has a diameter of 6 mm corresponding to the thickness of the rod (11). The rod (11) presents at its proximal end a hooking device (14) for the installation tool. It is typically a fixation device with a bayonet.

Figure 9:
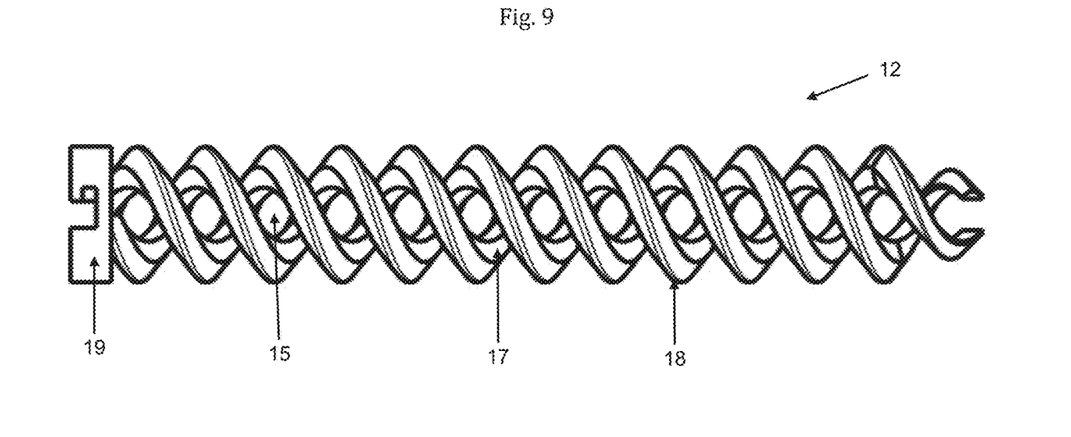
FIG. 9 represents an isometric view of the helical element (12) composed of two identical helices, of the curved implant (10) from FIG. 12.

The FIG. 9 presents a face view of a helical element (12) constituted by two helices thus by two helical elements having the same pitch, cores (17) and threads (18) of identical sizes and shapes. This double helical element (12) is aimed at being inserted in rotation on the rod (11) within the double helical groove (13) having a complementary shape and sizes. The double helical element (12) has a length of 67 mm between its proximal end and its distal end. Its external diameter is of 10 mm and the internal light (15) has a diameter of 4 mm.

Figure 10:
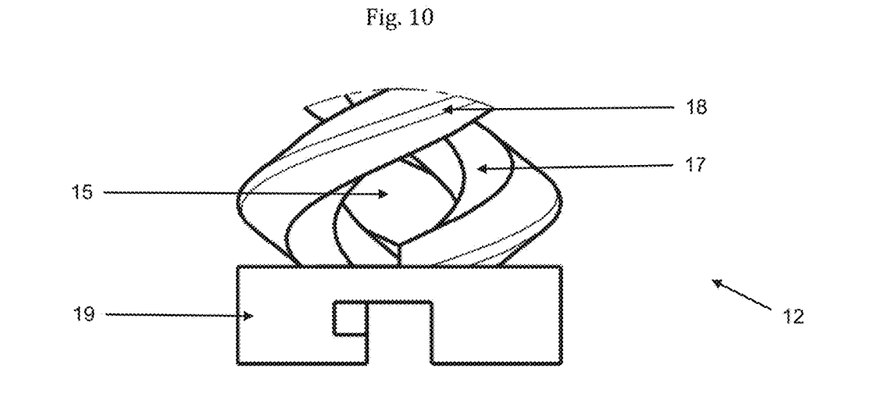
FIG. 10 represents a face view of the proximal end of the helical element (12) with its hooking system (19) and the base of the double helix of the curved implant (10) from FIG. 12.

The FIG. 10 describes in details the shape of the core (17) complementary to the flared shape of the helical groove (13) and the thread (18) is protruding according to a sharp angle in order to penetrate the bone and to fix itself firmly once the implant (10) is set up. The hooking of the helical element (13) to the installation tool is ensured by a bayonet hooking device (19). The core (17) and the thread (18) of the helical element (12) constitute guidance and anchoring devices of the helical element (13) within the helical groove (14) on one hand and the bone wall on the other hand.

Figure 11:
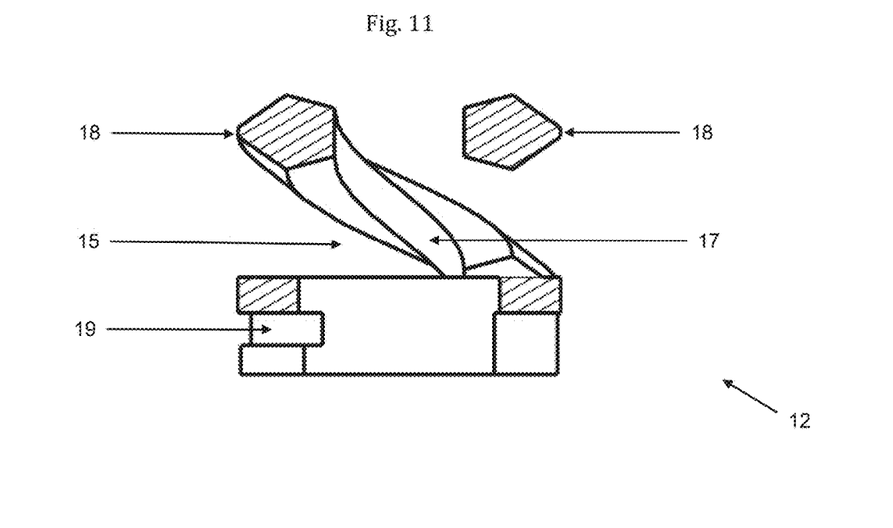
FIG. 11 represents a view in longitudinal section of the proximal end of the FIG. 10.

The FIG. 11 shows a cutting plan of the FIG. 10 thus one can see the shape of the cores of the double helical element (17) complementary to the flared shape of the helical grooves (13).

The size of the helical element, from the base of the core to the tope of the thread, is of 3 mm.

Figure 12:
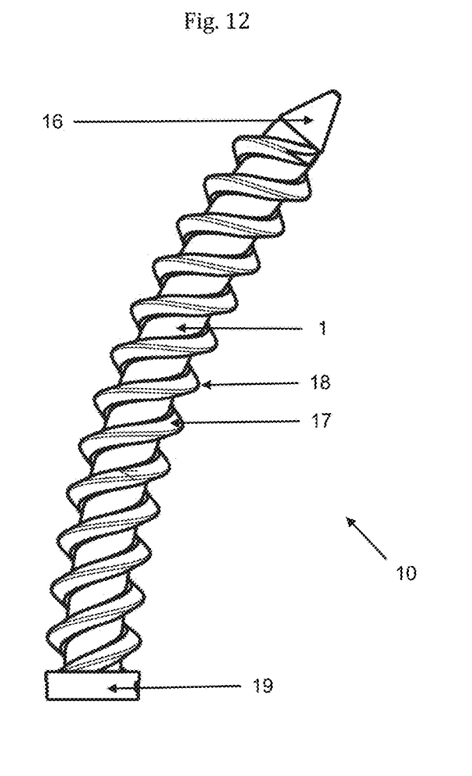
FIG. 12 represents a face view of the complete curved implant (10) forming a screw according to the invention described in details in the example below.
Figure 13:
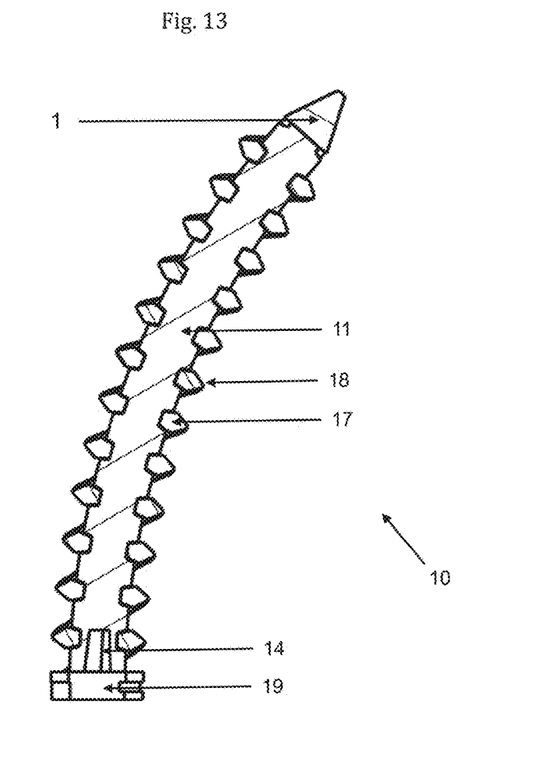
FIG. 13 represents a view in longitudinal section of the curved implant (10) of the FIG. 12.
Figure 14:
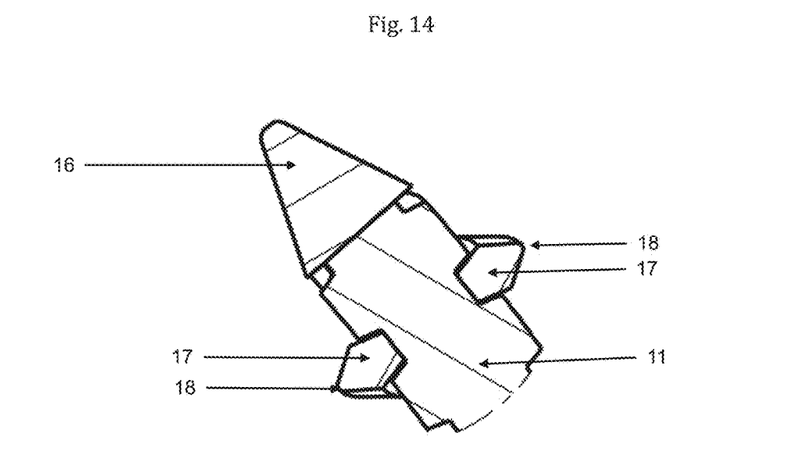
FIG. 14 represents the distal end of the curved implant (10) of the FIG. 12 with a head (16) in a conical shape.

The curved implant (10) is represented in a longitudinal view in FIG. 12. One see from the top to the bottom the conical head (16) of the rod (11), the two helical elements (12) each with its thread (18), each core (17) being inserted respectively in one helical groove (13), and the hooking device (19) allowing the installation and the withdrawal of the implant (10). The FIG. 13 is a view of a longitudinal section of the implant. Finally the FIG. 14 represents a view in longitudinal section of the distal end of the curved implant (10) and especially the conical head (16). One can also see the pentagonal shape of the helical elements (12) complementary to the flared form of the helical grooves (13) and the thread (18) aimed at penetrating the bone surface in order to anchor firmly the curved implant (10).

EXAMPLE 2

Surgical Implant for the Fixation of Vertebrae

The present example describes a surgical implant of a large size. This one takes again the technical elements of the implant (10) according to the fitting detailed above in example 1 and has a developed length of 140 mm describing an arc of 89.1° and of 90 mm radius.

EXAMPLE 3

Surgical Implant for the Fixation of Vertebrae

The present example describes a surgical implant of a small size. This one takes again the technical elements of the implant (10) according to the fitting detailed above in example 1 and has a developed length of 35 mm describing an arc of 22° and of 90 mm radius.

EXAMPLE 4

The table below describes the correspondence between developed length of the surgical implant (1, 10) according to the invention and the value of the arc angle in function of the radius of the circle in which said arc fits.

One skilled in the art will not have any problem to choose a size for the implant and an adapted curve in function of the size and the geometry of the bone elements to solidarize.

TABLE 1 values of the arc angle (en °) in function of the developed length of the implant and the circle radius for a constant curvature.

| Length (mm) | Radius (mm) | | | | |
|---|---|---|---|---|---|
| | R30 | R60 | R90 | R120 | R150 |
| L 20 | 38.2 | 19.1 | 12.7 | 9.5 | 7.6 |
| L 35 | 66.8 | 33.4 | 22.3 | 16.7 | 13.4 |
| L 70 | 133.7 | 66.8 | 44.5 | 33.4 | 26.7 |
| L 90 | 171.9 | 85.9 | 57.3 | 43.0 | 34.4 |
| L 110 | | 105.0 | 70.0 | 52.5 | 42.0 |
| L 120 | | 114.6 | 76.4 | 57.3 | 45.9 |
| L 140 | | 133.7 | 89.1 | 66.8 | 53.5 |
| L 160 | | 152.8 | 101.9 | 76.4 | 61.1 |
| L 180 | | 172.0 | 114.6 | 86.0 | 68.8 |

The invention claimed is:

1. Surgical implant for the fixation of at least two bone elements of a patient, comprising:
    a curved rod configured to be firstly inserted in a bore practised within the at least two bone elements, said curved rod defining a longitudinal axis which is curved in a relaxed state of the curved rod; and
    at least one distinct helical element configured to be mounted on said rod, the at least one distinct helical element including a single filled solid element of a helical shape forming plural coils,
    wherein the at least one distinct helical element forms a helical space extending along the at least one helical element from an innermost surface of the at least one helical element to an outermost surface of the at least one helical element, and
    wherein a portion of an outer surface of the curved rod is located within the helical space.

2. Surgical implant according to claim 1, wherein:
    said rod comprises, on its external surface, as many guidance elements in the shape of a helical groove as said at least one helical element said guidance elements each presenting an opening in a direction of one of the bone elements and
    each of the at least one distinct helical element includes a core having a shape and sizes complementary to the shape and sizes of at least one guidance element in order to be able to fit and slide within said at least one guidance element in the shape of a helical groove and one element present on the whole or part of the core length and protruding by the opening in the direction of the bone element.

3. Surgical implant according to claim 2, further comprising at least one anchoring element in the form of a thread.

4. Surgical implant according to claim 2, wherein the depth of the at least one helical groove is not constant on its whole length.

5. Surgical implant according to claim 1, wherein the rod is realized in one or several biocompatible materials that are flexible.

6. Surgical implant according to claim 1, wherein only certain portions of the rod are flexible.

7. Surgical implant according to claim 1, further comprising a blocking device of the at least one helical element in a desired position on the rod.

8. Surgical implant according to claim 1, comprising at least one hooking device allowing the installation and the withdrawal of the rod and of the at least one helical element.

9. Surgical implant according to claim 1, wherein the surgical implant has a length ranging between 35 mm and 140 mm and fits in an arc of circle ranging between 15 degrees and 90 degrees.

10. Method for the fixation of at least two adjacent bone elements that implement a surgical implant according to claim 1, said method comprising:
    boring a bore having characteristics previously defined by the surgeon in function of the bone elements to solidarize using a boring tool, then
    inserting the rod in the bore using an installation tool under medical radioscopy, then
    inserting each of the at least one distinct helical element on said rod using an installation tool allowing to instigate separately or simultaneously the different components of helical movement to said at least one helical element, and
    blocking the helical element on the rod in the desired position using a blocking device.

11. Method according to claim 10, wherein the method for fixation of at least two adjacent bone elements comprises the fixation of at least two adjacent vertebrae.

12. A kit for the implementation of the method of claim 10, comprising the surgical implant, the boring tool, the installation tool for the rod and the installation tool for the helical element.

13. Surgical implant configured for the fixation of at least two adjacent vertebrae of a patient, comprising:
    a curved rod that represents at least one helical groove, said curved rod defining a longitudinal axis which is curved in a relaxed state of the curved rod, said curved rod configured to be inserted firstly in a boring practised in the at least two vertebrae, and
    at least one distinct helical element configured to be inserted secondly on said rod within the at least one helical grooved, and of which a core presents a shape that is complementary to a shape of the helical groove, the assembly when set up forming a screw, the at least one distinct helical element including a single filled solid element of a helical shape forming plural coils,
    wherein the at leat one distinct helical element forms a helical space extending along the at least one helical element from an innermost surface of the at least one helical element to an outermost surface of the at least one helical element, and
    wherein a portion of an outer surface of the curved rod is located within the helical space.

14. Surgical implant according to claim 13, wherein the curved rod further presents a distal end that carries a head and a proximal end equipped with a hooking device; and that the at least one helical element presents further a thread and its proximal end is equipped with a hooking device; the at least one helical element being intended to be inserted in rotation on the rod once set up.

15. Surgical implant for the fixation of at least two adjacent vertebrae of a patient according to claim 13, wherein
    the at least one helical groove includes two helical grooves, said curved rod being configured to be inserted firstly in a boring practised in the at least two vertebrae, and the at least one distinct helical element includes two distinct helical elements configured to be inserted secondly on said rod within the two helical groove, and of which the cores presents a shape that is complementary to the shape of the helical grooves, the assembly when set up forming a screw.

16. Surgical implant according to claim 13, wherein the surgical implant has a developed length between 35 mm and 140 mm and is comprised in a circular arc between 15 degrees and 90 degrees.

\* \* \* \* \*